(12) United States Patent
Tsurui et al.

(10) Patent No.: US 7,952,045 B2
(45) Date of Patent: May 31, 2011

(54) MATERIAL PIECE SCOOPING DEVICE

(75) Inventors: Takafumi Tsurui, Hyogo (JP);
Masaharu Fujiwara, Hyogo (JP);
Hiroyuki Nagasawa, Hyogo (JP);
Akihiro Kanaya, Hyogo (JP); Junichi Kusumoto, Hyogo (JP)

(73) Assignees: Minatogawa Kinzoku Test Piece Manufacturing Co., Ltd., Hyogo (JP);
Kobe Material Testing Laboratory Co., Ltd, Hyogo (JP); Kyushu Electric Power Co., Inc., Fukuoka (JP)

(*) Notice: Subject to any disclaimer, the term of this patent is extended or adjusted under 35 U.S.C. 154(b) by 739 days.

(21) Appl. No.: 11/922,584

(22) PCT Filed: Mar. 14, 2006

(86) PCT No.: PCT/JP2006/305015
§ 371 (c)(1),
(2), (4) Date: Dec. 20, 2007

(87) PCT Pub. No.: WO2007/105308
PCT Pub. Date: Sep. 20, 2007

(65) Prior Publication Data
US 2010/0012627 A1    Jan. 21, 2010

(51) Int. Cl.
*B23H 1/00* (2006.01)
(52) U.S. Cl. ..................... 219/69.2; 219/69.15
(58) Field of Classification Search ............... 219/69.16, 219/69.17, 69.2, 69.15; 376/260; 83/919
See application file for complete search history.

(56) References Cited

U.S. PATENT DOCUMENTS

| | | | | |
|---|---|---|---|---|
| 3,806,691 A | * | 4/1974 | Roach | 219/69.15 |
| 4,773,799 A | * | 9/1988 | Guironnet | 408/150 |
| 4,948,933 A | * | 8/1990 | Thompson | 219/69.2 |
| 5,268,550 A | * | 12/1993 | Blocquel et al. | 219/69.17 |
| 5,569,393 A | * | 10/1996 | Reinhart et al. | 219/69.15 |
| 5,818,006 A | * | 10/1998 | Habel et al. | 219/69.17 |
| 5,861,608 A | * | 1/1999 | Thompson | 219/69.2 |
| 5,897,793 A | * | 4/1999 | Chavez | 219/69.2 |

FOREIGN PATENT DOCUMENTS

| | | |
|---|---|---|
| JP | 63-146743 U | 9/1988 |
| JP | 63-231238 A | 9/1988 |

(Continued)

OTHER PUBLICATIONS

Machine translation of Japan Patent No. 8-108,319, Sep. 2010.*

(Continued)

*Primary Examiner* — Geoffrey S Evans
(74) *Attorney, Agent, or Firm* — Kubotera & Associates, LLC

(57) ABSTRACT

A material piece scooping device, which extracts a material piece from a surface of an object to be scooped by cutting electric discharges between an electric discharge electrode and the object to be scooped, includes a rotation drive section 40, an arm portion 30 driven by the rotation drive section to rotate around a rotational axis X, an electrode holder 20 supported by the arm portion, and an electric discharge electrode 10 detachably mounted on the electrode holder. A sliding section for sliding the arm portion in a direction perpendicular to the rotational axis and an arm length adjusting section for adjusting a length of the arm portion from the rotational axis thereof are provided, so as to adjust a trajectory of the electric discharge electrode as the arm portion rotates. The material piece can be scooped from the object along a line of the trajectory gnawing into the object.

7 Claims, 6 Drawing Sheets

FOREIGN PATENT DOCUMENTS

| | | |
|---|---|---|
| JP | 06-33046 U | 4/1994 |
| JP | 07-159295 A | 6/1995 |
| JP | 8-108319 A * | 4/1996 |
| JP | 9-155646 A * | 6/1997 |
| JP | 09-155646 A | 6/1997 |
| JP | 09-218139 A | 8/1997 |
| JP | 10-002988 A | 1/1998 |
| JP | 10-076427 A | 3/1998 |
| JP | 2001-079658 A | 3/2001 |

OTHER PUBLICATIONS

Machine translation of Japan Patent No. 9-155,646, Sep. 2010.*

* cited by examiner

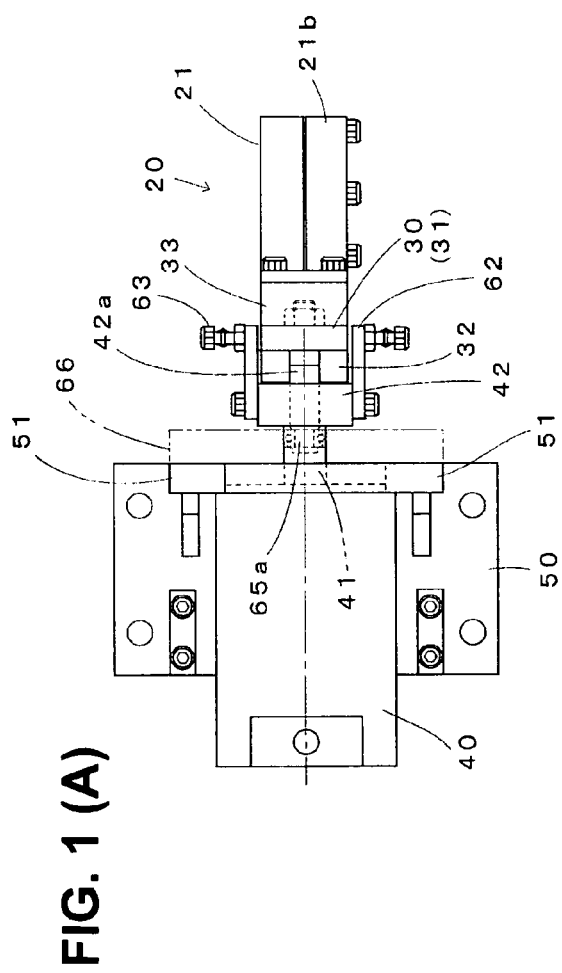
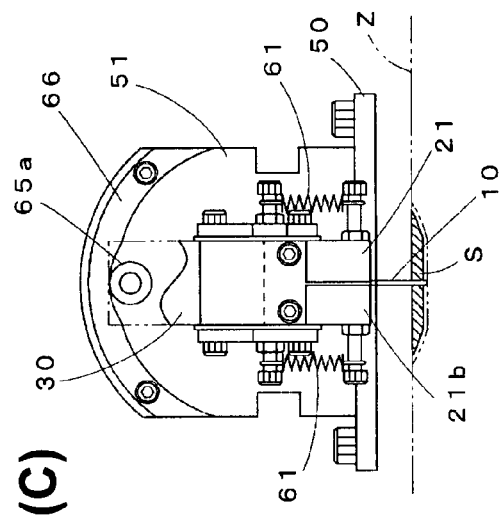
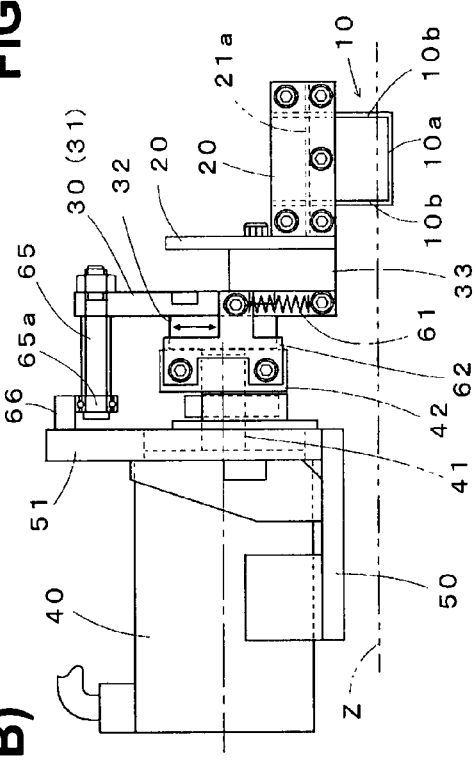
FIG. 1(A)
FIG. 1(B)
FIG. 1(C)

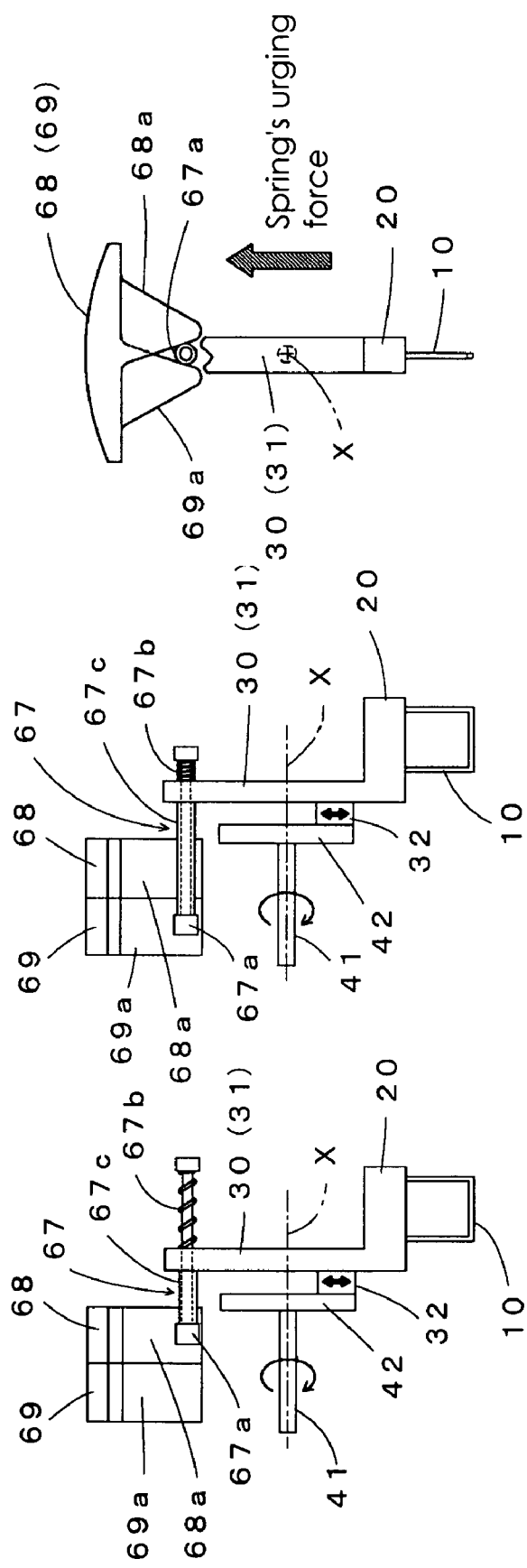

MATERIAL PIECE SCOOPING DEVICE

TECHNICAL FIELD

The present invention relates a material piece scooping device. More particularly, the present invention relates to a material piece scooping device capable of sampling a material piece or removing a defective portion from a pipe or other constituent member of a facility currently functioning in an operating facility, while minimizing damage on the facility and minimizing deformation of the constituent member of the facility due to an extracting operation or accompanying heat.

BACKGROUND ART

In a facility such as a power generating plant in operation, where operating conditions are relatively harsh or safety must be ensured, it is necessary to monitor deterioration in strength of a constituent member used in the facility in operation. Further, it is necessary to predict a remaining service life of a constituent member and carry out maintenance service at a proper timing.

For this purpose, when it is intended to continue the operation of the facility, it is a common practice to employ a nondestructive testing method for inspecting the constituent member in the facility.

On the other hand, instead of the nondestructive testing, a material may be taken out as a test piece from the constituent member of the facility. In this case, a member may be replaced as a whole before taking a test piece therefrom, or a large member may be transported to a factory where a test piece can be taken from the member.

Accordingly, a test piece or other material piece is taken after transporting the member to be tested to a facility equipped with a sampling device, rather than transporting a sampling device to a field and taking a test piece from the constituent member of the facility in the field.

Also, in a case that a constituent member of the facility has a defective portion in a surface thereof, it is necessary to remove the defective portion from the member, so that the removed portion can be tested as required. However, it is difficult to provide a device which can be carried to the field and is capable of readily removing the defective portion from the constituent member of an operating facility.

The test piece or other material piece taken out of the constituent member of the facility is subjected to mechanical or other test. Accordingly, if the test piece is changed in nature thereof due to deformation during the extracting operation or the accompanying heat, it is difficult to accurately evaluate the sample. According, it is necessary to prevent the deformation of the constituent member of the facility during the extracting operation or the accompanying heat as much as possible.

To this end, for example, an electric discharge machine may be used to sample a test piece or remove a defective portion.

The electric discharge machine is a device for machining an object by generating an electric discharging between the device and the object. With the device, it is possible to reduce an area of the object subjected to machining strain within a relatively narrow region.

Patent Reference 1: Japanese Patent Publication No. 2001-79658
Patent Reference 2: Japanese Patent Publication No. 10-76427,
Patent Reference 3: Japanese Patent Publication No. 10-2988,
Patent Reference 4: Japanese Patent Publication No. 9-218139,
Patent Reference 5: Japanese Patent Publication No. 9-155646,
Patent Reference 6: Japanese Patent Publication No. 7-159295

In the nondestructive testing method described above, it is not possible to measure an actual mechanical strength. Accordingly, it is difficult to estimate deterioration of the constituent member of the operating facility and predict the life.

A conventional test piece sampling device is a fixed type of a heavy weight, and is suitable for such an application in which the test piece sampling device is transported to a sampling site and is set for an operation of sampling a constituent member of an operating facility.

When the electric discharge machine is used to sample a test piece or other material piece, it is possible to minimize undergoing mechanical and thermal deformation on the test piece thus obtained. However, the conventional electric discharge machine is a machining tool in nature, and a principal object thereof is not to obtain a material piece. Therefore, the electric discharge machine is not convenient for sampling a material piece.

When a conventional device disclosed in Patent References 1 to 6 is used to obtain a material piece, it is necessary to repeat an operation of moving an electric discharge electrode several times until the material piece is sampled, thereby causing problems related to an operating procedure and an operating time. In addition, the conventional device can rotate and move the electric discharge electrode simply along an arc-shaped trajectory. There has not been any device capable for conveniently and easily adjusting a trajectory of an electric discharge electrode.

Accordingly, an object of the present invention is to solve the problems described above and provide a material piece scooping device with a compact construction capable of sampling a test piece or removing a defective portion from a pipe and other constituent member of a facility at a site, while minimizing deformation caused by an extracting operation or accompanying heat.

MEANS TO SOLVE THE PROBLEMS

In order to solve the problems described above, according to a first feature of the present invention, a material piece scooping device generates an electric discharge between an electric discharge electrode and an object to be scooped disposed to oppose the electric discharge electrode. Accordingly, a material piece is successively removed and scooped from a surface of the object to be scooped. The material piece scooping device comprises a rotation drive section; an arm portion driven by the rotation drive section to rotate around an rotational axis; an electrode holder supported by the arm portion; and the electric discharge electrode detachably mounted on the electrode holder. Further, a sliding section is provided for sliding the arm portion in a direction perpendicular to the rotational axis, and an arm portion length adjusting section is provided for adjusting a length of the arm portion from the rotational axis. Accordingly, it is possible to adjust a trajectory of the electric discharge electrode when the arm portion is driven to rotate. As a result, it is possible to scoop or extract the material piece from the surface of the object to be scooped along a line of the trajectory of the electric discharge electrode gnawing into the object to be scooped.

According to a second feature of the present invention, in addition to the first feature described above, in the material piece scooping device, the sliding section comprises a slide guide mounted on a rotary stage which is driven to rotate on a side of the rotation drive section, and a sliding member which is secured on the arm portion and is guided in the direction perpendicular to the rotational axis by the slide guide.

According to a third feature of present invention, in addition to the first or second feature described above, in the material piece scooping device, the arm portion length adjusting section has an urging spring for urging the arm portion to slide in the direction perpendicular to the rotational axis, and a tracing guide disposed along a circle drawn by the rotating arm portion for contacting with the arm portion so as to guide the arm portion thereby to adjust the arm portion length during a rotation thereof.

According to a fourth feature of the present invention, in addition to the third feature described above, the material piece scooping device is provided with a plurality of tracing guides having different guide surfaces, so that it is possible to select and detachably mount one of the tracing guides.

According to a fifth feature of the present invention, in addition to the third or fourth feature described above, in the material piece scooping device, a plurality of the tracing guides is combined and mounted.

According to a sixth feature of the present invention, in addition to one of the first to fifth features described above, in the material piece scooping device, the arm portion is driven to move linearly or reciprocally.

According to a seventh feature of the present invention, in addition to one of the first to sixth features described above, in the material piece scooping device, the arm portion length adjusting section maintains a constant depth of the trajectory of the electric discharge electrode with respect to the object to be scooped, so as to scoop the material piece having a constant thickness.

According to the invention described in the first feature, the arm portion is driven by the rotation drive section to rotate around the rotational axis. Accordingly, the electrode holder mounted on the arm portion accordingly rotates while carrying the electric discharge electrode. As the rotation of the arm portion proceeds very slowly, the electric discharge is generated between the electric discharge electrode and the object to be scooped which is disposed to face the electric discharge electrode near the rotating direction thereof, thereby removing the material from the object to be scooped along the trajectory of the electric discharge electrode. Accordingly a separating surface is formed and expands along the trajectory of the electric discharge electrode, so that eventually a portion of the object to be scooped separated by the separating surface is taken out. The material piece can be used for various purposes such as a test, or can be discarded as a defective portion, and the likes. The object to be scooped may also be subjected to a post-treatment according to a shape of the removed portion.

The device can be set at an intended portion of the object to be scooped in the facility to remove the material from the surface of the object to be scooped along the trajectory of the electric discharge electrode. At this time, the material piece having a predetermined shape can be removed from the target portion by controlling the trajectory of the electric discharge electrode.

Since the electric discharge electrode has a predetermined width in the direction perpendicular to the direction of rotation, the width roughly corresponds to a width of the material piece.

A radius of rotation of the electric discharge electrode can be adjusted during the rotation thereof by enabling the arm portion to slide in the direction perpendicular to the rotational axis and controlling the length of the arm portion by the arm portion length adjusting section. Accordingly, it is possible to change the trajectory of the electric discharge electrode from an arc shape to a more flat shape or vice versa, in accordance to a thickness and a shape of the object to be scooped, a kind of test to be conducted, a condition of a defective portion to be removed, a shape of the material piece to be obtained, and other conditions. As a result, the material piece having a desired shape can be extracted by adjusting the trajectory of the electric discharge electrode gnawing through the object to be scooped.

Thus, according to the invention described in the first feature, the material piece can be extracted from the surface of the target portion of the object to be scooped in a field. Also because the material piece is extracted by the electric discharge machining, changes in nature of the material piece caused during the extracting operation can be minimized by setting an optimum discharge condition, and the material piece can be subjected to precision tests. Thus, the material piece can be subjected to various mechanical tests, physical tests, and chemical tests, so as to obtain information such as a fatigue progress, a life estimate, and timing for maintenance service. It is also possible to prevent the object to be scooped from undergoing deterioration of the material.

The material piece can also be scooped automatically as the arm portion rotates, thereby making the operation easy. For a portion where a stress concentration is expected or the material is welded in a large structure, a residual stress can be measured through attaching a strain gage and locally extracting a portion.

Further, the device is provided with the rotation drive section, the arm portion, the electrode holder, the electric discharge electrode, the arm portion sliding section, the arm portion length adjusting section, and the like. Accordingly, it is possible to constitute the device relatively easily in a compact construction, and to transport the device to the field and set up easily.

According to the invention described in the second feature, in addition to the effects of the configuration in the first feature as described above, the sliding section comprising the sliding member mounted on the arm portion, the rotary stage provided on the rotation drive section side and the slide guide makes it possible to move the arm portion in the direction perpendicular to the rotational axis easily and reliably with a simple configuration.

According to the invention described in the third feature, in addition to the effects of the configuration in the first or second feature as described above, the arm portion rotates while being urged by the urging spring in the direction perpendicular to the rotational axis and makes contact with the tracing guide at the circumferential position, so that the sliding position in the direction perpendicular to the rotational axis can be easily controlled.

Thus, the length of the arm portion can be adjusted easily and reliably during rotation with a simple configuration, by means of the arm portion length adjusting section which has the urging spring and the tracing guide.

According to the invention described in the fourth feature, in addition to the effects of the configuration in the third feature as described above, the device has such a configuration that has the plurality of tracing guides which have different guide surfaces from which a proper one is selected and detachably mounted, so that the tracing guide of an appropriate shape for the shape of the object to be scooped and the shape of the material piece can be selected and attached, thus making it possible to extract the material piece of the desired shape and easily obtain the object to be scooped from which a portion of the desired shape has been removed.

According to the invention described in the fifth feature, in addition to the effects of the configuration in the third or fourth feature as described above, the configuration of mounting the plurality of tracing guides provides the advantage that material pieces of various shapes can be scooped by means of a combination of the existing tracing guides, without the need to prepare a new tracing guide.

According to the invention described in the sixth feature, in addition to the effects of the configuration in any one of the first to fifth features as described above, the configuration of driving the arm portion to make one-way or reciprocal motion makes it possible that, in case the arm portion is driven to make one-way motion, a material piece can be scooped easily from the object to be scooped by the rotating motion in that direction. In case the arm portion is driven to make reciprocal motion, one additional step of operation is required for extraction, although a material piece of more complicated shape can be scooped.

According to the invention described in the seventh feature, in addition to the effects of the configuration in any one of the first to sixth features as described above, the configuration in which depth of the trajectory of the electric discharge electrode gnawing in the object to be scooped is controlled to be constant by means of the arm portion length adjusting section, so as to keep the thickness of the material piece taken out constant, makes it possible to prevent the object to be scooped from being gouged too deep. Also the capability of keep the thickness of the material piece taken out constant means that a test piece suitable for mechanical test can be sampled, and that unnecessary portion which is not used in the test being taken out of the object to be scooped can be minimized. The capability to prevent the object to be scooped from being gouged too deep is important for ensuring safety of the member.

BRIEF DESCRIPTION OF THE DRAWINGS

FIGS. 1(A) to 1(C) show a material piece scooping device according to a first embodiment of the present invention, wherein FIG. 1(A) is a plan view thereof, FIG. 1(B) is a front view thereof, and FIG. 1(C) is a side view thereof.

FIGS. 3(A) and 3(B) are schematic explanatory diagrams of a mechanism of the material piece scooping device according to the first embodiment of the present invention, wherein FIG. 3(A) is a front view thereof, and FIG. 3(B) is a side view thereof.

FIGS. 4(A) to 4(C) are explanatory diagrams of a material piece extracting operation of the material piece scooping device according to the first embodiment of the present invention, wherein FIG. 4(A) is a view showing the extracting operation at the beginning thereof, FIG. 4(B) is a view showing the extracting operation in the middle thereof, and FIG. 4(C) is a view showing the extracting operation at the end.

FIGS. 5(A) to 5(C) are schematic explanatory diagrams of a mechanism of a material piece scooping device according to a second embodiment of the present invention, wherein FIGS. 5(A) and FIG. 5(B) are front views thereof, and FIG. 5(C) is a side view thereof.

FIGS. 6(A) to 6(D) are explanatory diagrams of a material piece extracting operation of the material piece scooping device according to the second embodiment of the present invention, wherein FIG. 6(A) is a view showing an operation of a first tracing guide at the beginning of the extracting operation, FIG. 6(B) is a view showing the operation of the first tracing guide at the end of the extracting operation, FIG. 6(C) is a view showing an operation of a second tracing guide at the beginning of the extracting operation, and FIG. 6(D) is a view showing the operation of the second tracing guide at the end of the extracting operation.

DESCRIPTION OF REFERENCE NUMERALS

Figure 2:
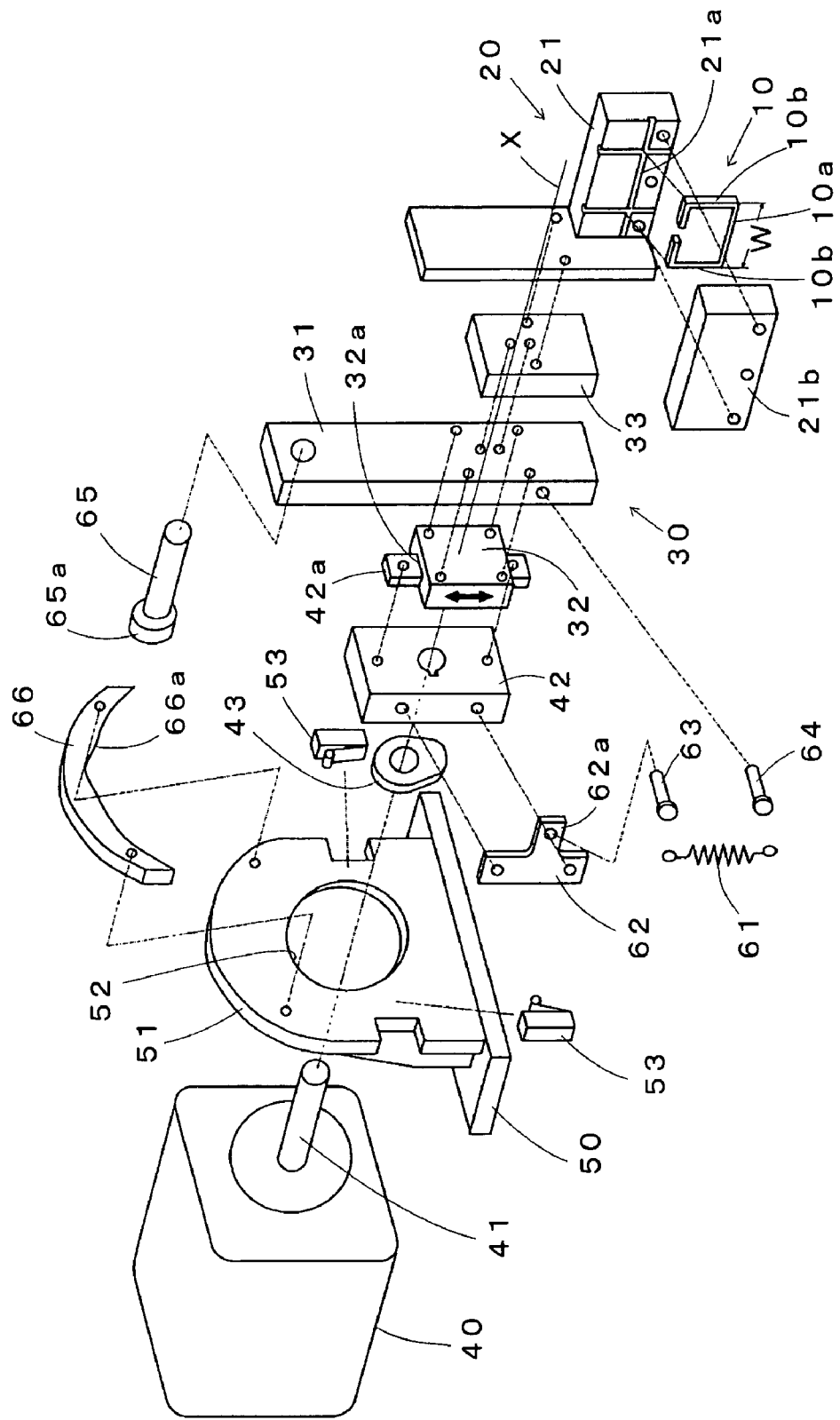
FIG. 2 is an exploded perspective view of the material piece scooping device according to the first embodiment of the present invention.

10 Electric discharge electrode
10a Horizontal portion
10b Vertical portion
20 Electrode holder
21 Holding section
21a Mounting groove
21b Lid
30 Arm portion
31 Main body
32 Sliding member
32a Sliding groove
33 Insulator block
40 Rotation drive section
41 Rotation drive shaft
42 Rotary stage
42a Slide guide
43 Limit switch activator piece
50 Base
51 Vertical wall
52 Opening
53 Limit switch
61 Urging spring
62 Spring mounting plate
62a Protruding piece
63 Spring set bolt
64 Spring set bolt
65 Tracing bolt
65a Roller
66 Tracing guide
66a Guide surface
67 Tracing bolt
67a Roller
67b Urging spring
67c Spacer
68 First tracing guide
68a Guide surface
69 Second tracing guide
69a Guide surface
S Material piece
W Width of electric discharge electrode
X Rotational axis
Z Object to be scooped

BEST MODE FOR CARRYING OUT THE INVENTION

First, the material piece scooping device according to the first embodiment will be described.

With reference made to FIGS. 1(A) to 1(C) and FIG. 2, the material piece scooping device of the present invention comprises an electric discharge electrode 10, an electrode holder 20 whereon the electric discharge electrode 10 can be detachably mounted, an arm portion 30 which holds the electrode holder 20, and rotation drive section 40 which causes the arm portion 30 to rotate around an rotational axis X.

The rotation drive section 40 is constituted from a motor such as a servo motor. The rotation drive section 40 is fixed on a base 50, and a rotation drive shaft 41 of the rotation drive section 40 protrudes through an opening 52 formed in a vertical wall 51 of the base 50.

The rotation drive shaft 41 of the rotation drive section 40 has the rotary stage 42 secured at the distal end thereof, the rotary stage 42 being driven to rotate together with the rotation drive shaft 41. The rotary table 42 is pivoted at the center thereof on the rotation drive shaft 41 and rotates around it.

The rotation drive shaft 41 of the rotation drive section 40 also has a limit switch activator piece 43 secured thereon at a mid position. The limit switch activator piece 43 makes contact with a pair of limit switches 53 mounted on the base 50 so as to turn on the limit switch 53, thereby keeping the rotation drive shaft 41 of the rotation drive section 40 from rotating further. The limit switch activator piece 43 and the limit switch 53 play a role of restricting the rotation of the arm portion 30 within a certain range.

The arm portion 30 causes the electric discharge electrode 10 to move along a circle about the rotational axis of the arm portion 30.

The arm portion 30 is constituted so as to be driven by the rotation drive shaft 41 of the rotation drive section 40 to rotate around the rotational axis X which corresponds to the rotation drive shaft 41, while sliding in a direction perpendicular to the rotational axis X.

The arm portion 30 has the sliding member 32 secured on one side of an main body 31 which is formed in an elongated rectangular shape, and holds the electrode holder 20 on the other side via an insulation block 33.

The sliding member 32 has a slide groove 32a. The rotary table 42 has, on the side thereof opposite to the slide groove 32a, the slide guide 42a which passes through the rotational axis X that is the center of rotation of the rotary table 42 and extends in the direction perpendicular to the rotational axis X. The slide guide 42a is fitted in the slide groove 32a of the sliding member 32 so as to be capable of sliding relative to each other. Accordingly, the arm portion 30 can move sliding in direction perpendicular to the rotational axis X.

The sliding member 32 having the slide groove 32a and the slide guide 42a mounted on the rotary table 42 constitute the sliding section.

The arm portion 30 is urged by the urging spring 61 in the direction perpendicular to the rotational axis X. Specifically, the arm portion 30 is urged by the urging spring 61 in the sliding direction of the sliding section (32, 32a, 42a).

The urging spring 61 is set between the spring set bolt 63 which is provided on the protruding piece 62a of the pair of spring mounting plates 62 secured on both sides of the rotary table 42, and the spring set bolt 64 provided on both sides of the main body 31 of the arm portion 30. The protruding piece 62a of the spring mounting plate 62 extends from the rotary table 42 toward the main body 31 of the arm portion 30, and the spring set bolt 63 is disposed just above the spring set bolt 64 on the side face of the main body 31 of the arm portion 30.

Provided above the main body 31 of the arm portion 30 is the tracing bolt 65 having the roller 65a provided at the distal end thereof. In correspondence to the tracing bolt 65, the tracing guide 66 is provided on the vertical wall 51 of the base 50.

The tracing bolt 65 is disposed in parallel to the rotational axis X of the arm portion 30, and the roller 65a disposed at the distal end thereof is in contact with the guide surface 66a formed on the bottom of the tracing guide 66. The roller 65a moves along the guide surface 66a as the arm portion 30 rotates, while being pressed by the urging spring 61 against the guide surface 66a.

The tracing guide 66 is disposed on the circle drawn by the rotation of the arm portion 30. The guide surface 66a of the tracing guide 66 determines the trajectory along which the electric discharge electrode 10 moves. As the roller 65a moves along the profile of the guide surface 66a, the sliding position of the arm portion 30 in the direction perpendicular to the rotational axis X during rotation is determined, so that length of the arm portion 30 is adjusted. That is, length of the arm portion 30 from the rotational axis X to the position where the electric discharge electrode 10 is held is adjusted during rotation. As the length of the arm portion 30 is adjusted during rotation, the trajectory of the electric discharge electrode 10 is controlled.

The urging spring 61, the tracing bolt 65, the tracing guide 66 and the like (more specifically, the urging spring 61, the spring set bolts 63, 64, the tracing bolt 65 and the tracing guide 66) constitute the arm length adjusting means that adjusts the length of the arm from the rotational axis X thereof.

The electrode holder 20 is held on the arm portion 30 via the insulation block 33. The electrode holder 20 has a holding member 21 which sandwiches the electric discharge electrode 10 so as to detachably hold it. The electric discharge electrode 10 is fitted in a mounting groove 21a of the holding member 21 and is clamped by the lid 21b, so as to be held. As the arm portion 30 rotates, the electrode holder 20 revolves around the rotational axis X.

The electric discharge electrode 10 is formed in C shape and is constituted so as to keep a constant width W in the direction perpendicular to the rotating direction (parallel to the rotational axis X). Specifically, the electric discharge electrode 10 has C shape consisting of a horizontal portion 10a having the width W and vertical portions 10b extending from both ends of the horizontal portion 10a. When the trajectory traced by the electric discharge electrode in accordance to the rotation of the arm 10 meets the object Z to be scooped, the material is removed from the portions of the object Z to be scooped which are close to and facing the horizontal portion 10a and the vertical portions 10b. In the area of the object Z to be scooped which is enclosed by the configuration of the electric discharge electrode, on the other hand, the material is not removed. As a result, the material piece S having the width of W is taken out of the object Z to be scooped.

While the electric discharge electrode 10 shown in the drawing has the horizontal portion 10a and the vertical portions 10b crossing each other with an angle of 90 degrees, the horizontal portion 10a and the vertical portions 10b may also be connected in U shape. The angle between the horizontal portion 10a and the vertical portions 10b is not limited to 90 degrees, and may be larger than or smaller than 90 degrees.

With reference made to FIGS. 3(A) and 3(B) and FIGS. 4(A) to 4(C) which simplify the material piece scooping device, mechanism and operation of the material piece scooping device according to the first embodiment will be described below.

When the rotation drive shaft 41 of the rotation drive section 40 is driven to rotate, the rotary stage 42 rotates accordingly, which in turn causes the main body 31 of the arm portion 30 to rotate. As the arm portion 30 rotates, the electric discharge electrode 10 moves around the rotational axis X via the electrode holder 20. The arm portion 30 can be caused to slide by the sliding section (32, 32a, 42a), while the roller 65a moves while being pressed against the guide surface 66a by the arm length adjusting means (61, 65, 66), so that length of the arm is adjusted in accordance to the surface irregularity of the guide surface 66a. As the length of the arm portion 30 is adjusted during rotation, trajectory of the electric discharge electrode 10 is changed from the arc shape in the course of the rotation.

Figure 3:
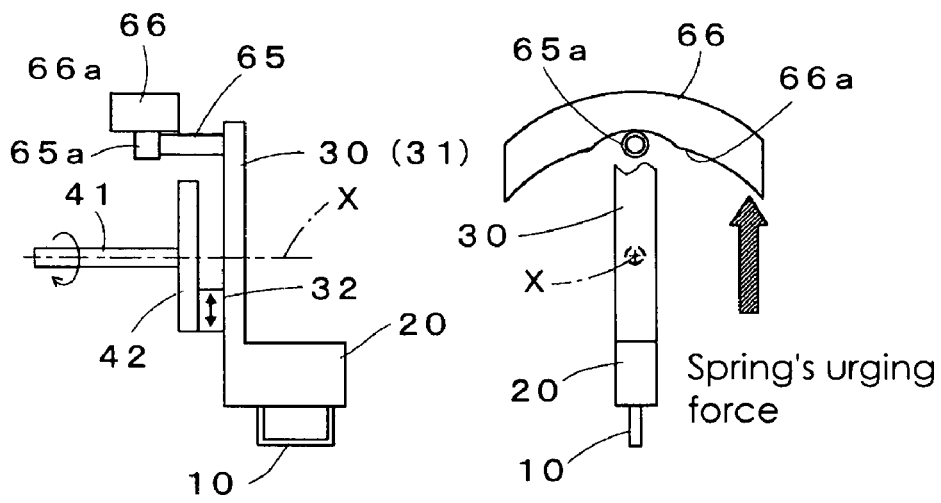

As shown in FIG. 3(B), the guide surface 66a of the tracing guide 66 has an arc-shaped surface as a whole with the mid portion being deeper than both sides. When the roller 65a passes the deep portion of the curved surface, length of the arm for rotating the electric discharge electrode 10 is controlled to be shorter. As a result, the electric discharge electrode 10 moves along such a trajectory that is arc-shaped at the start and the end which are connected by a boat-shaped portion which is proximate to straight line.

Figure 4:
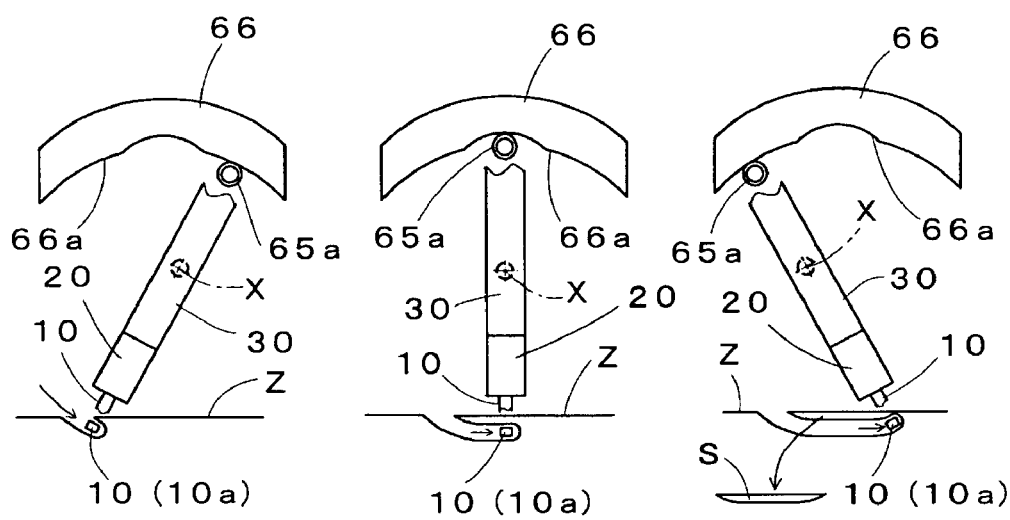

After starting to gnaw into the object Z to be scooped along the arc-shape trajectory as shown in FIG. 4(A), the electric discharge electrode 10 proceeds at a substantially constant depth as shown in FIG. 4(B), before emerging from within the object Z to be scooped along the arc-shape trajectory as shown in FIG. 4(C). As a result, the material piece S having the boat shape is taken out of the object Z to be scooped.

As the guide surface 66a of the tracing guide 66 is formed in such a shape as the electric discharge electrode 10 traces the boat-shaped trajectory as described above, the material piece S having the boat shape with width of W is taken out of the object Z to be scooped. Since the thickness of the material piece S having the boat shape can be kept constant, the material piece can be easily prepared for mechanical test and other tests. Also because gnawing into the object Z to be scooped can be carried out at a far smaller depth in comparison to a case of, for example, taking out an arc-shaped material piece, adverse effects on the strength and safety of the object Z to be scooped can be minimized even when it is a part of a facility currently in operation.

Various shapes of the guide surface 66a of the tracing guide 66 can be employed in accordance to the shape of the material piece S to be scooped and the thickness and the shape of the object Z to be scooped. However, shapes of the guide surface 66a of the tracing guide 66 is preferably such that the electric discharge electrode 10 gnaws into the object Z to be scooped with a larger angle at the start of gnawing and the end of gnawing while, in the mid portion, gnawing along a path parallel to the surface of the object Z to be scooped.

With reference made to FIGS. 5(A) to 5(C) and FIGS. 6(A) to 6(D), the material piece scooping device according to the second embodiment of the present invention will be described below. The device of the second embodiment has a configuration substantially the same as the material piece scooping device of the first embodiment, except for the configuration of the tracing bolt 67, the first tracing guide 68, and the second tracing guide 69.

The second embodiment employs the electric discharge electrode 10 and the electrode holder 20 which have dimensions a little different from those of the first embodiment.

In the second embodiment, the tracing bolt 67 is provided to penetrate through the arm portion 30, and the roller 67a is provided at the distal end thereof. The urging spring 67b is provided on the tracing bolt 67 at a position behind the arm portion 30, so as to always urge the tracing bolt 67 backward (toward the rear end). A spacer 67c is detachably mounted on the tracing bolt 67 at a position in front of the arm portion 30, so that the spacer can be replaced with another one. FIG. 5(A) shows such a configuration as the spacer 67c having small length is used so that the roller 67a is brought into contact with the guide surface 68a which is formed on the bottom of the first tracing guide 68. FIG. 5(B) shows such a configuration as the spacer 67c having large length is used so that the roller 67a is brought into contact with the guide surface 69a which is formed on the bottom of the second tracing guide 69.

The second embodiment is a case which uses the first tracing guide 68 and the second tracing guide 69 in combination. Specifically, the second tracing guide 69 and the first tracing guide 68 are placed one on another and detachably mounted by screwing or the like on the vertical wall 51 of the base 50.

The guide surfaces 68a, 68b formed on the bottom of the first tracing guide 68 and the second tracing guide 69 are disposed symmetrically on the right and left, respectively. The guide surfaces 68a, 69a are both formed so as to protrude downward in substantially V shape. In this embodiment, the sloped surface on the left side of the substantially V shape that constitutes the guide surface 68a of the first tracing guide 68 is actually used as the guide surface. In the second tracing guide 69, the sloped surface on the right side of the substantially V shape that constitutes the guide surface 69a of the second tracing guide 69 is used as the guide surface.

Now the device of the second embodiment will be described with reference to FIG. 6(A), FIG. 6(B), FIG. 6(C) and FIG. 6(D) which show the operation of the device.

Figures 6A, 6B, 6C, 6D:
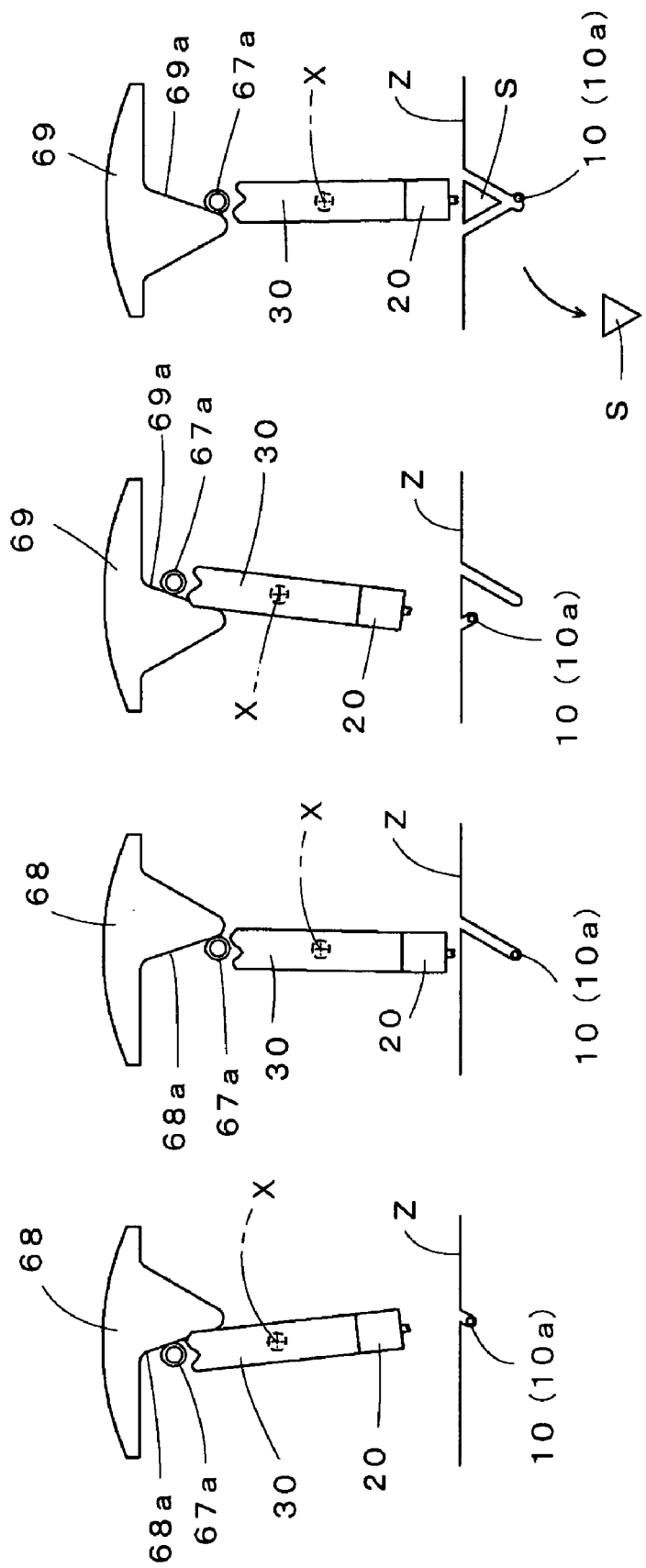

First, the shorter spacer 67c shown in FIG. 5(A) is used and set so that the roller 67a of the tracing bolt 67 makes contact with the guide surface 68a of the first tracing guide 68. The arm portion 30 is set so as to rotate clockwise first. This causes the electric discharge electrode 10 to start gnawing into the object Z to be scooped in an arc-shaped trajectory while turning clockwise as shown in FIG. 6(A). The electric discharge electrode turns clockwise until the arm portion 30 is disposed at right angles to the surface of the object Z to be scooped. The arm portion 30 rotates while being guided by the substantially V-shaped guide surface 68a of the first tracing guide 68, and length of the arm is adjusted by sliding in the direction perpendicular to the rotational axis X. Accordingly, in this embodiment, the electric discharge electrode 10 gnaws into the object Z to be scooped in a straight path to the left downward from the surface of the object. When the electric discharge electrode has proceeded to the state shown in FIG. 6(B), the electric discharge machining is once stopped and the electric discharge electrode 10 is removed from the object Z to be scooped by rotating the arm portion 30 in reverse direction or otherwise.

After the electric discharge electrode 10 has been removed from the object Z to be scooped, the spacer 67c of the tracing bolt 67 is changed from the shorter one shown in FIG. 5(A) to the longer one shown in FIG. 5(B). Accordingly, the roller 67a of the tracing bolt 67 makes contact with the guide surface 69a of the second tracing guide 69.

Then the arm portion 30 is rotated counterclockwise. This causes the electric discharge electrode 10 to start gnawing into the object to be scooped Z in an arc-shaped trajectory while turning counterclockwise as shown in FIG. 6(C). The electric discharge electrode turns counterclockwise until the arm portion 30 is disposed at right angles to the surface of the object Z to be scooped. The arm portion 30 rotates while being guided by the substantially V-shaped guide surface 69a of the first tracing guide 69, and length of the arm is adjusted by sliding in the direction perpendicular to the rotational axis X. Accordingly, in this embodiment, the electric discharge electrode 10 gnaws into the object Z to be scooped in a straight path to the right downward from the surface of the object. When the electric discharge electrode has proceeded to the state shown in FIG. 6(D), rotation of the arm portion 30 is stopped and the electric discharge machining is stopped. In this process, a material piece S having V-shaped cross section is taken out of the object Z to be scooped.

Such a configuration is also within the scope of the present invention that, as in the second embodiment, besides combining the two tracing guides 68, 69, the arm portion 30 is driven to move reciprocally to take out the material piece S so that, by causing the arm portion 30 (the electric discharge electrode 10) to move reciprocally rather than one-way motion, thereby to take out the material piece S.

INDUSTRIAL APPLICABILITY

The material piece scooping device of the present invention is capable of taking out a material piece from the surface of various structures including tubes, solid material, etc. made of various metallic materials. More particularly, the material piece scooping device is capable of sampling a material piece or removing a defective portion from pipes and other constituent member of a facility which are currently functioning in the operating facility, while minimizing the damage caused on the facility and minimizing the deformation of the constituent member of the facility due to the extracting operation or the accompanying heat, thus offering great industrial utility.

The invention claimed is:

1. A material piece scooping device for extracting a material piece from a surface of an object to be scooped through generating an electric discharge between an electric discharge electrode and the object to be scooped so as to successively remove the material piece from the object to be scooped that is disposed to oppose the electric discharge electrode, comprising:
   a rotation drive section;
   an arm portion driven to rotate around a rotational axis thereof with the rotation drive section;
   an electrode holder supported with the arm portion for detachably mounting the electric discharge electrode thereon;
   a sliding section for sliding the arm portion in a direction perpendicular to the rotational axis; and
   an arm portion length adjusting section for adjusting length of the arm portion from the rotational axis so as to adjust a trajectory of the electric discharge electrode when the arm portion is driven to rotate so that the material piece is scooped from the surface of the object to be scooped along a line where the trajectory of the electric discharge electrode crosses the object to be scooped.

2. The material piece scooping device according to claim 1, wherein said sliding section is disposed on the rotation drive section, said sliding section including a slide guide mounted on a rotary stage driven to rotate and a sliding member secured on the arm portion, said slide guide guiding the sliding member in the direction perpendicular to the rotational axis.

3. The material piece scooping device according to claim 1, wherein said arm portion is driven to move linearly or reciprocally.

4. The material piece scooping device according to claim 1, wherein said arm portion length adjusting section is adapted to adjust a depth of the trajectory of the electric discharge electrode cutting into the object to be scooped at a constant level so that the material piece to be scooped has a constant thickness.

5. The material piece scooping device according to claim 1, wherein said arm portion length adjusting section includes an urging spring for urging the arm portion to slide in the direction perpendicular to the rotational axis, and a tracing guide provided along a rotational circle of the arm portion for contacting with and guiding the arm portion so as to adjust the length of the arm portion during rotation of the arm portion.

6. The material piece scooping device according to claim 5, further comprising a plurality of tracing guides having different guide surfaces, one of the tracking guides being selected and detachably mounted.

7. The material piece scooping device according to claim 5, wherein said tracing guide is mounted at each of a plurality of locations.

* * * * *